United States Patent [19]

Neuwelt

[11] Patent Number: 5,124,146

[45] Date of Patent: Jun. 23, 1992

[54] DIFFERENTIAL DELIVERY OF THERAPEUTIC AGENTS ACROSS THE BLOOD BRAIN BARRIER

[75] Inventor: Edward A. Neuwelt, Portland, Oreg.

[73] Assignee: The State of Oregon Acting by and through the State Board of Higher Education on Behalf of Oregon Health Sciences University, Portland, Oreg.

[21] Appl. No.: 644,331

[22] Filed: Jan. 22, 1991

Related U.S. Application Data

[63] Continuation of Ser. No. 122,024, Nov. 18, 1987, abandoned.

[51] Int. Cl.$^5$ ............................................. A61K 37/04
[52] U.S. Cl. .................................... 424/85.8; 514/922
[58] Field of Search ........................................ 424/85.8

[56] References Cited

U.S. PATENT DOCUMENTS

| | | | |
|---|---|---|---|
| 4,351,831 | 9/1982 | Growdon et al. | 424/199 |
| 4,363,793 | 12/1982 | Blau et al. | 424/1 |
| 4,479,932 | 10/1984 | Bodor | 424/9 |
| 4,540,564 | 9/1985 | Bodor | 424/9 |
| 4,622,218 | 11/1986 | Bodor | 424/9 |
| 4,624,846 | 11/1986 | Goldenberg | 424/1.1 |
| 4,634,586 | 1/1987 | Goodwin et al. | 424/1.1 |

OTHER PUBLICATIONS

Neuwelt et al., "Characterization of a New Model of $G_{M2}$-Gangliosidosis (Sandhoff's Disease) in Korat Cats," *J. Clin. Invest.* 76:482-490 (1985).
Neuwelt et al., "Osmotic Blood-Brain Barrier Opening to IgM Monoclonal Antibody in the Rat," *Am. J. Physiol.* 250:R873-R883 (1986).
Neuwelt et al., "Cerebrovascular Permeability and Delivery of Gentamicin to Normal Brain and Experimental Brain Abscess in Rats," *J. Neurosurg.* 61:430-439 (1984).
Neuwelt et al., "Osmotic Blood-Brain Barrier Modification: Monoclonal Antibody, Albumin, and Methotrexate Delivery to Cerebrospinal Fluid and Brain," *Neurosurg.* 17:419-423 (1985).
Sage, "Blood-Brain Barrier: Phenomenon of Increasing Importance to the Imaging Clinician," *J. Am. J. Roentgenol.* 138:887-898 (1982).
Neuwelt et al., "Growth of Human Lung Tumor in the Brain of the Nude Rat as a Model to Evaluate Antitumor Agent Delivery Across the Blood-Brain Barrier," *Cancer Research* 45:2827-2833 (1985).
Greig, "Chemoteraphy of Brain Metastases: Current Status," *Cancer Treatment Reviews* 11:157-186 (1984).
Sharkey et al., "Factors Influencing Anti-Antibody Enhancement of Tumor Targeting with Antibodies in Hamsters with Human Colonic Tumor Xenografts," *Cancer Research* 48:2005-2009 (1988).
Hiesiger et al., "Opening the Blood-Brain and Blood-Tumor Barriers in Experimental Rat Brain Tumors: The Effect of Intracarotid Hyperosmolar Mannitol on Capillary Permeability and Blood Flow," *Annals of Neurology* 19:50-59 (1986).
Neuwelt et al., "Permeability of Human Brain Tumor to 99mTC-glucoheptonate and 99mTc-albumin," *J. Neurosurg.* 65:194-198 (1986).
Neuwelt et al., "Increased Delivery of Tumor-Specific Monoclonal Antibodies to Brain After Osmotic Blood-Brain Barrier Modification in Patients with Malanoma Metastatic to the Central Nervous System," *Neurosurgery* 20:885-895 (1987).
Barranger et al., "Modification of the Blood-Brain Barrier: Increased Concentration and Fate of Enzymes Entering the Brain," *Proc. Natl. Acad. Sci. U.S.A.* 76:481-485 (1979).
Blasberg et al., "Regional Localization of a Glioma-Associated Antigen Defined by Monoclonal Antibody 81C6 *in Vivo:* Kinetics and Implications for Diagnosis and Therapy," *Cancer Research* 47:4432-4443 (1987).
Smith et al., "Treatment of Life-Threatening Digitalis Intoxication with Digoxin-Specific Fab Antibody Fragments," *New Engl. J. of Med.* 307:1357-1362 (1982).
Blasberg et al., "Concurrent Measurements of Blood Flow and Transcapillary Transport in ASV-Induced Experimental Brain Tumors: Implications for Brain Tumor Chemotherapy," *J. Pharmacol. Exp. Ther.* 231:724-735 (1984).
Groothuis et al., "Regional Blood Flow and Blood-to-Tissue Transport in Five Brain Tumor Models," in Rosenblum et al. (eds.), *Prog. Exp. Tumor Res.* 27:132-153 (1984).

*Primary Examiner*—Merrell C. Cashion, Jr.
*Assistant Examiner*—Choon Koh
*Attorney, Agent, or Firm*—Klarquist, Sparkman, Campbell, Leigh & Whinston

[57] ABSTRACT

A method for the delivery of therapeutic agents across the blood brain barrier is disclosed which utilizes drug neutralization technology, and the selective permeability of the blood brain barrier (BBB). During and after the formation of brain lesions, the BBB becomes increasingly permeable. To treat these conditions, a therapeutically effective amount of a selected drug is administered having a molecular weight and other characteristics allowing passage of the drug through the modified BBB. Thereafter, a neutralizing material specific to the drug is administered. The neutralizing material has a high molecular weight and/or some other characteristic(s) which prevent its passage through the modified BBB. The neutralizing material binds to or reacts with the excess drug circulating outside the BBB, in order to prevent the manifestation of drug toxicity problems.

7 Claims, No Drawings

DIFFERENTIAL DELIVERY OF THERAPEUTIC AGENTS ACROSS THE BLOOD BRAIN BARRIER

This invention was made with support by the Preuss Foundation and with Government support by the Veterans Administration and under Grant No. 31770 awarded by the National Institutes of Health. The Government has certain rights in this invention.

This is a continuation of application Ser. No. 07/122,024, filed Nov. 18, 1987, now abandoned.

BACKGROUND OF THE INVENTION

The present invention generally relates to a method for delivering therapeutic agents into the brain, and more specifically to such a method in which the therapeutic agents are delivered across the blood brain barrier.

In treating diseases of the brain and central nervous system, it would be advantageous to have a practical method for delivery of a drug across the blood brain barrier (BBB). The BBB is a capillary barrier comprising a continuous layer of tightly bound endothelial cells. These cells permit a low degree of transendothelial transport, and exclude molecules in the blood from entering the brain on the basis of molecular weight and lipid solubility, as described in Neuwelt, E. A., "Is There A Therapeutic Role For Blood-Brain Barrier Disruption" *Ann. Int. Med.* 93: 137-139, 1980. For example, the blood brain barrier normally excludes molecules with a molecular weight greater than 180 daltons. In addition, the lipid solubility of molecules is a major controlling factor in BBB passage.

Considerable research has been conducted relating to the BBB and its permeability. Articles involving permeability of the BBB include:

1. "Chemotherapy of brain metastases: Current status" Greig, N. H., *Cancer Treatment Reviews*, 11: 157-186 (1984).
2. "Cerebrovascular permeability and delivery of gentamicin to normal brain and experimental brain abscess in rats", Neuwelt, E. A., et al, *Journal of Neurosurgery*, 61: 430-439 (1984).
3. "Blood-Brain Barrier: Phenomenon of Increasing Importance to the Imaging Clinician", Sage, M. R., *American Journal of Roentgenology*, 138: 887-898 (1982).
4. "Opening the Blood-Brain and Blood-Tumor Barriers in Experimental Rat Brain Tumors: The Effect of Intracarotid Hyperosmolar Mannitol on Capillary Permeability and Blood Flow", Hiesinger, E. M. et al, *Annals of Neurology*, 19: 50-59 (1986).

The foregoing articles discuss the permeability characteristics of the BBB in terms of lipid solubility, ionization fraction, protein binding and/or the molecular weight of foreign molecules. As specifically described by Sage, the function of the BBB is to maintain the homeostasis of the neuronal environment. The continuity produced by the tight junctions between individual cells of the BBB enables the cerebrocapillary endothelium to act like a plasma membrane. Small molecules (m.w. <200 daltons) having a high degree of lipid solubility and low ionization at physiological pH are freely passed through the BBB. In addition, the BBB allows water to move in either direction in order to maintain equal osmotic concentrations of solutes in the extracellular cerebral fluid.

However, recent research has shown that the BBB may become increasingly permeable during the development or onset of brain tumors, vascular lesions, or abscesses. As discussed by Sage, the cerebrocapillary endothelium has a close investment by a glial sheath. Destruction of the glial sheath by mitotic activity may make the capillaries therein more permeable. Tumors appear to stimulate the proliferation of abnormal capillaries by releasing specific angiogenic factors in the brain.

The unique biological aspect of the BBB is an important focus in treating central nervous system disorders. While the interendothelial junctions between the cells of the BBB are normally designed to keep potentially noxious substances away from the brain, this condition changes during the formation of brain abscesses, inflammation, and/or tumors, as described above. For example, tests have shown that experimental allergic encephalomyelitis (EAE) may cause an immune reaction which increases the permeability of the BBB. Alvoode, E. C. et al, "Experimental Allergic Encephalomyelitis: A Useful Model For Multiple Sclerosis", *Prog. Clin. Biol. Res.*, Vol. 146, Alan, R., Liss Co., New York, 1984. One explanation for the increased permeability of the BBB at the onset of EAE involves the capability of endothelial cells of the cerebrovasculature system to act as antigen presenting cells (APCs), thus attracting T-cells and aiding their penetration across the BBB. Accordingly, it has been found that brain endothelial cells are capable of expressing histocompatibility antigens on their surfaces.

Another possible explanation for the increase in the permeability of the BBB during the onset of lesions involves the ability of the brain under these circumstances to generate vasoactive substances, as described in Black, K. L., "Leukotrienes Increase Blood-Brain Barrier Permeability Following Intraparenchymal Injections In Rats." *Ann. Neurol.*, 18: 349-351, 1985. Brain lipids are rich in arachidonic acid which may be released by trauma to the brain tissue, e.g., by neoplastic invasion or ischemia. Black has shown experimentally that arachidonic acid and leukotrienes can increase BBB permeability when injected directly into the rat brain. Leukotriene content of the brain tissue correlates significantly with the amount of edema surrounding various CNS neoplasms, and it is conceivable that leukotrienes released from the damaged brain contribute to BBB disruption and vasogenic edema in CNS neoplasia.

Likewise, inflammation of brain tissue in immune-mediated CNS disease might possibly cause release of arachidonic acid and leukotrienes which would increase the permeability of the BBB. A further discussion of increased BBB permeability with reference to nervous system disorders, including infections, inflammatory conditions, neoplasms, and ischemia is presented in Fishman, R. A., *Cerebrospinal Fluid in Diseases of the Nervous System*, W. B. Saunders Co., Philadelphia, London, Toronto, 1980; Tourtelotte, W. "On Cerebrospinal IgG Quotients In Multiple Sclerosis and Other Diseases. A Review And A New Formula To Estimate The Amount Of IgG Synthesized Per Day By the Central Nervous System", *J. Neurol. Sci.*, 10: 279-304, 1970.

As described herein, the increased permeability of the BBB caused by brain lesions can be used in the administration of drugs designed to treat these problems. However, care must be taken to insure that the use of drugs under these conditions does not result in physiological toxicity due to drug overdosage. This frequently occurs since large doses of drugs are often required to treat lesions such as abscesses or tumors of the brain, especially if multiple abscesses or tumors are involved.

One method for treating brain tumors which includes a control mechanism to prevent drug overdosage is disclosed in the above-cited *Cancer Treatment Reviews* article. Page 164 of the article discusses a technique involving the administration of high doses of methotrexate followed within 24-36 hours by an additional technique called "leucovorin rescue". Methotrexate chemically prevents tumor proliferation by binding almost irreversably to the enzyme dihydrofolate reductase which prevents the formation of the coenzyme tetrahydrofolate, an essential material for DNA synthesis. In order to control an overdose of methotrexate, leucovorin is added which supplies the tissues with additional tetrahydrofolate, resulting in diminished patient toxicity without eliminating the anti-tumor effect of methotrexate. However, use of this method is not possible for most drugs.

Thus, a need currently exists for a method designed to administer therapeutic agents across the BBB for the treatment of brain lesions, while avoiding problems associated with systemic overdosage. The present invention represents a method for accomplishing these goals.

SUMMARY OF THE INVENTION

It is an object of the present invention to provide a method for the delivery of therapeutic agents across the blood brain barrier in order to treat brain lesions (i.e. tumors, vascular lesions, abscesses and similar disorders).

It is another object of the invention to provide a method for the delivery of therapeutic agents across the BBB in which delivery is made possible through the increased permeability of the BBB caused by brain lesions, abscesses or similar disorders.

It is another object of the invention to provide a method for the delivery of therapeutic agents across the blood brain barrier which minimizes physiological side effects associated with other treatment methods.

It is a further object of the invention to provide a method for the delivery of therapeutic agents across the blood brain barrier which is readily applicable to a wide variety of brain disorders.

It is an even further object of the invention to provide a method for the delivery of therapeutic agents across the blood brain barrier which avoids problems associated with drug overdosage.

To accomplish these objectives, a method for the delivery of therapeutic agents across the blood brain barrier is disclosed which utilizes drug neutralization technology and the selective permeability of the blood brain barrier. During and after the formation of brain lesions, the blood brain barrier (BBB) becomes increasingly permeable. A blood-brain barrier having an increased permeability due to the presence of a brain lesion is referred to herein as a "blood-brain lesion barrier." To treat these conditions, a therapeutically effective amount of a selected drug is administered to the bloodstream of a subject. The drug is selected to have a molecular weight and/or lipid solubility allowing passage of the drug through the modified BBB. Thereafter, a substance designed to neutralize the drug (e.g., an antibody specific for the drug) is administered. The neutralizing material is selected to have a sufficiently high molecular weight or have other chemical characteristics which prevent its passage through the modified BBB. The neutralizing agent reacts with or binds to the drug circulating outside of the BBB, so that the drug is rendered inactive and/or more readily removed through renal clearance. Since the neutralizing agent cannot pass or passes very poorly through the altered BBB, the amount of drug in the brain is relatively unaffected. Use of this procedure results in an effective method for administering therapeutic agents across the BBB for the treatment of brain lesions while avoiding toxicity problems inherent in other treatment methods.

These and other objects, features and advantages of the invention will be described in the detailed description of a preferred embodiment presented below.

DETAILED DESCRIPTION

The present invention involves a method for treating a variety of brain and central nervous system diseases, including CNS tumors, cerebrovascular lesions, CNS infections, and degenerative processes of the CNS. All of these diseases are characterized by the formation of brain lesions. As previously described, the endothelial cells of the BBB capillary tissues normally permit a low degree of transendotheial passage of foreign materials. However, research has discovered that brain lesions cause an increase in BBB permeability. This increase allows the passage of larger molecular weight materials across the BBB. For example, the BBB will normally prevent molecules larger than 180 daltons from entry into the brain. During and after the onset of brain lesions, the BBB will permit the increased passage of molecules having a molecular weight of about 500 to 1,000 daltons. Examples of drugs which may pass through the modified BBB i.e., blood-brain lesion barrier include the antimetabolite methotrexate, the antibiotic gentamicin, and fluorescein.

Because of the modified BBB structure during and after lesion formation, it is now possible to administer therapeutic agents which would not pass through a normal BBB. Following administration, it is important that therapeutic agents circulating outside the BBB do not reach toxic levels. This is often a problem since high doses of drugs used to treat brain and CNS lesions are often required, especially if multiple lesions are involved.

To control drug toxicity, the present invention involves administration of an "inactivating" or "neutralizing" material (e.g., drug antibody) specific to the drug initially administered. The neutralizing material will have characteristics designed to prevent its passage through the modified BBB, thus ensuring that concentrations of the drug inside the BBB remain active. Such characteristics can include lipid solubility, molecular weight, electrical charge, and others.

In terms of molecular weight, neutralizing materials having a molecular weight in excess of about 1,000 daltons typically will not effectively pass through the modified BBB. After administration, such neutralizing material will typically act by binding with the drug circulating outside the BBB, thereby forming a complex conjugate which is either inactive and/or cleared from the circulatory system.

Similarly, certain neutralizing agents of lower molecular weight will be prevented from crossing the BBB due to some other characteristics such as lipid solubility or electrical charge.

Antibodies or antibody fragments (i.e., Fab or (Fab')$_2$) usable in the invention are prepared conventionally in either a polyclonal or monoclonal form. Thus, suitable antibodies for numerous therapeutic agents, including methotrexate and gentamicin are readily available.

In summary, the method of the present invention utilizes the modified character of the BBB caused by lesion formation to deliver therapeutic agents into tissues of the brain, while insuring that subsequently administered drug neutralizing substances remain outside of the BBB. As described above, this enables circulating amounts of the drug to be precisely controlled.

Administration of a therapeutic agent, followed by administration of a neutralizing material to reduce toxicity, across the BBB in a subject animal having a brain lesion is described below in the following example:

EXAMPLE

A. Method and Materials

Adult, female, Sprague-Dawley rats at six days post inoculation intracerebrally with $2.0 \times 10^6$ cfu *E. coli* bacteria were anesthetized with sodium pentobarbital (50 mg/kg, intraperitoneal). A catheter filled with heparinized sodium chloride was tied into the right external carotid artery. Evans blue and fluorescein were administered intravenously (2.0%, 2 ml/kg and 10%, 0.12 ml, respectively) to evaluate the integrity of the abscess barrier.

Subsequently, dosages of $^{125}$I-gentamicin were administered intravenously. One hour thereafter, a preantibody serum sample was collected to evaluate the non-specific binding of gentamicin to serum proteins. Antigentamicin antibody (0.06 ml antisera+0.2 ml PBS) or nonimmune sera, was administered intravenously. Fifteen minutes later, a post antibody serum sample was collected to evaluate the extent of binding for circulating gentamicin. The rat was then sacrificed by perfusion with 0.9% NaCl to clear the vascular bed of radioactivity. Tissue samples consisting of abscess (AB), brain around abscess (BAA), brain distant to the abscess (BFA), and contralateral hemisphere (LH) were weighed and then homogenized in 0.5 ml of saline. To precipitate immune complexes, 2 ml of isopropyl alcohol was added to aliquots of tissue homogenates and 1 ml of alcohol to serum, centrifuged for 15 minutes at $1200 \times g$, and the resulting fractions counted for activity.

B. Results and Conclusions

Summaries of the data obtained in the above experiment are described as follows in Tables I and II.

TABLE I

| | \multicolumn{7}{c}{Immune Serum} | |
|---|---|---|---|---|---|---|---|
| | AB | BAA | BFA | LH | Pre | Post | P-Per | Cl |
| \multicolumn{9}{c}{Rat G-70; Dose: $6.0 \times 10^6$ cpm} |
| cpm/gm | 7298 | 3292 | 2159 | 1501 | | | | 99 |
| % Bound | 52 | 42 | 54 | 457 | 22 | 97 | 43 | |
| % Del. Dose | .12 | .06 | .04 | .03 | | | | |
| \multicolumn{9}{c}{Rat G-73; Dose: $13.0 \times 10^6$ cpm} |
| cpm/gm | 17,074 | 5703 | 1436 | 1000 | | | | 97 |
| % Bound | 44 | 31 | 49 | 49 | 22 | 96 | 75 | |
| % Del. Dose | .13 | .04 | .01 | .01 | | | | |
| \multicolumn{9}{c}{Rat G-80; Dose: $13.0 \times 10^6$ cpm} |
| cpm/gm | 43,305 | 12,413 | 2895 | 2684 | | | | 92 |
| % Bound | 49 | 45 | 55 | 55 | 36 | 94 | 70 | |
| % Del. Dose | .14 | .04 | .01 | .01 | | | | |
| \multicolumn{9}{c}{Rat G-85; Dose: $11.8 \times 10^6$ cpm} |
| cpm/gm | 11,728 | 6823 | 2488 | 1245 | | | | 95 |
| % Bound | 63 | 59 | 60 | 52 | 26 | 96 | 79 | |
| % Del. Dose | .10 | .06 | .02 | .01 | | | | |
| \multicolumn{9}{c}{Rat G-87; Dose: $14.0 \times 10^6$ cpm} |
| cpm/gm | 12,694 | 5694 | 4428 | 814 | | | | 94 |
| % Bound | 73 | 61 | 68 | 41 | 24 | 96 | 75 | |
| % Del. Dose | .09 | .04 | .03 | .01 | | | | |
| \multicolumn{9}{c}{Rat G-88; Dose: $14.1 \times 10^6$ cpm} |
| cpm/gm | 15,254 | 8457 | 4073 | 1012 | | | | 96 |
| % Bound | 56 | 53 | 65 | 50 | 23 | 96 | 77 | |
| % Del. Dose | .11 | .06 | .03 | .01 | | | | |

LEGEND:
AB: Abscess
BAA: Brain Around Abscess
BFA: Brain Distant to the Abscess
LH: Left or Non Abscess Bearing Hemisphere
Pre: Precipitable radioactivity from serum prior to antibody administration
Post: Precipitable radioactivity from serum after antibody administration
P-Per: Precipitable radioactivity from serum after perfusion of rat
Cl: Percent clearance of activity from serum
$\frac{\text{Post-perfusion}}{\text{Pre-perfusion}} \times 100$
cpm/gm: Counts per minute of radioactivity per gram tissue
% Bound: Percent precipitable radioactivity from tissue sample
% Del. Dose: Percent delivered dose of radioactivity per gram of tissue

TABLE II

| | AB | BAA | BFA | LH | Pre | Post | P-Per | Cl |
|---|---|---|---|---|---|---|---|---|
| \multicolumn{9}{c}{Non Immune Serum} |
| \multicolumn{9}{c}{Rat G-89; Dose: $18.4 \times 10^6$ cpm} |
| cpm/gm | 12,304 | 11,236 | 5920 | 4991 | | | | 84 |
| % Bound | 44 | 45 | 48 | 47 | 26 | 27 | 21 | |
| % Del. Dose | .07 | .06 | .03 | .03 | | | | |
| \multicolumn{9}{c}{Rat G-90; Dose: $18.4 \times 10^6$ cpm} |
| cpm/gm | 22,460 | 9417 | 3038 | 1389 | | | | 86 |
| % Bound | 30 | 44 | 43 | 50 | 22 | 21 | 3 | |
| % Del. Dose | .12 | .05 | .02 | .01 | | | | |
| \multicolumn{9}{c}{Rat G-91; Dose: $20 \times 10^6$ cpm} |
| cpm/gm | 17,789 | 10,247 | 2036 | 1180 | | | | 85 |
| % Bound | 31 | 36 | 48 | 36 | 24 | 22 | 2 | |
| % Del. Dose | .09 | .05 | .01 | .01 | | | | |
| \multicolumn{9}{c}{MEAN VALUES} |
| \multicolumn{9}{c}{Immune Serum} |
| % Bound | 56 | 49 | 59 | 51 | 26 | 96 | 70 | 96 |
| Standard Error | 4 | 5 | 3 | 2 | 2 | .4 | 6 | 1 |
| % Del. Dose | 0.12 | 0.05 | 0.02 | 0.01 | | | | |
| Standard Error | 0.1 | .004 | .01 | .003 | | | | |
| \multicolumn{9}{c}{Non Immune Serum} |
| % Bound | 35 | 42 | 46 | 44 | 24 | 23 | 9 | 85 |
| Standard Error | 5 | 3 | 2 | 4 | 1 | 2 | 6 | .6 |
| % Del. Dose | 0.09 | 0.05 | 0.02 | 0.01 | | | | |
| Standard Error | .02 | .003 | .01 | .01 | | | | |

In rats given non-immune serum, the per cent of delivered dose per gram of tissue in abscess was 0.09% indicating the presence of a cerebral abscess. In brain around abscess (BAA), brain distant to abscess (BFA), and contralateral hemisphere (LH), the values were 0.05%, 0.02%, and 0.01%. These values indicate that in areas of increased vascular permeability (i.e., BBB incompetence), a marked elevation in drug delivery can be seen (cerebritic brain 0.09% versus normal brain 0.01%). Pre and post serum precipitation values of 24% and 23% indicate that gentamicin nonspecifically precipitates with serum proteins, and that the addition of non-immune serum does not alter precipitation characteristics. The precipitation of activity from brain tissues were 35% (AB), 42% (BAA), 46% (BFA), and 44% (LH). These values suggest that there is more nonspecific precipitation activity from the brain since serum nonspecific binding was appreciably lower.

In rats given anti-gentamicin antibody, the pre and post serum precipitation values of 26% and 96% indicate that sufficient antibody was administered to adequately bind a significant fraction of circulating drug. Again, the per cent delivered dose per gram of tissue data indicates the presence of a cerebral abscess (0.12% (AB) versus 0.01% (LH)). The precipitation of activity (% Bound) in the antibody-administered rats was high, as in the control group, but no difference could be seen between the abscess (56%) and normal brain (51%). This suggests that if the antibody had been able to penetrate the abscess, more precipitation should have been seen due to the addition of immunoprecipitation.

Having herein described a preferred embodiment of the invention, it will be anticipated that suitable modifications may be made by those skilled in the art that fall within the scope of the invention. Thus, the scope of the invention shall be only construed in accordance with the following claims.

What is claimed is:

1. A method for delivering a drug to a brain lesion in a warm-blooded animal subject, which subject having a brain with a blood-brain barrier and the brain lesion having a blood-brain lesion barrier, the method comprising the steps:
   (a) providing a drug to which the blood-brain barrier is at least partially permeable;
   (b) administering a dose of the drug to the subject at a site outside the blood-brain and blood-brain lesion barriers;
   (c) allowing a first portion of the administered dose of the drug to pass through the blood-brain lesion barrier, thereby leaving a second portion of the administered dose remaining outside the blood-brain lesion barrier;
   (d) providing a neutralizing agent having an ability to inactivate the drug and which is substantially incapable of passing through the blood-brain lesion barrier into the brain lesion; and
   (e) administering a dose of the neutralizing agent to the subject at a site outside the blood-brain and blood-brain lesion barriers so as to at least partially inactivate the second portion of the administered dose of the drug.

2. A method as recited in claim 1, wherein the administered dose of the drug is systemically toxic to the subject.

3. A method as recited in claim 2, wherein the neutralizing agent is administered to the subject before the subject experiences systemically toxic effects due to the drug.

4. A method as recited in claim 1, wherein the neutralizing agent comprises antibody molecules that bind the drug.

5. A method as recited in claim 1, wherein molecules of the drug have a smaller molecular weight than molecules of the neutralizing agent.

6. A method as recited in claim 1, wherein the drug is administered to the subject when said blood-brain lesion barrier has a greater permeability to the drug than said blood-brain barrier.

7. A method for delivering a systemically toxic drug to a brain lesion in a warm-blooded animal subject without the subject experiencing substantial systemic toxicity effects from the drug, which subject having a brain with a blood-brain barrier and a blood-brain lesion barrier, the blood-brain lesion barrier being at least partially permeable to the drug, the method comprising the steps:
   (a) administering a systemically toxic dose of the drug to the subject at a site outside the blood-brain and blood-brain lesion barriers;
   (b) allowing a first portion of the administered dose of the drug to pass through the blood-brain lesion barrier, thereby leaving a second portion of the administered dose at a systemically toxic concentration outside the blood-brain lesion barrier; and
   (c) before the subject experiences substantial toxic effects due to the second portion of the administered dose, administering to the subject at a site outside the blood-brain and blood-brain lesion barriers a neutralizing agent to which the blood-brain and blood-brain lesion barriers are substantially impermeable, the neutralizing agent having an ability to inactivate the drug, thereby reducing the systemically toxic concentration of the second portion of the administered dose of the drug.

* * * * *